United States Patent
Kadan

(12) 
(10) Patent No.: US 6,428,510 B1
(45) Date of Patent: Aug. 6, 2002

(54) DIAGNOSTIC NEEDLE ARTHROSCOPY AND LAVAGE SYSTEM

(76) Inventor: Jeffrey S. Kadan, 216 Via Linda Vista, Redondo Beach, CA (US) 90277

( * ) Notice: Subject to any disclaimer, the term of this patent is extended or adjusted under 35 U.S.C. 154(b) by 0 days.

(21) Appl. No.: 09/570,324

(22) Filed: May 12, 2000

Related U.S. Application Data

(63) Continuation-in-part of application No. 09/495,601, filed on Feb. 1, 2000.

(51) Int. Cl.$^7$ .............................................. A61M 5/178
(52) U.S. Cl. ..................... 604/164.04; 604/27
(58) Field of Search .............................. 604/27, 164.04, 604/30, 33, 35, 43, 44, 45, 506, 511; 606/53, 167, 185; 600/101, 104

(56) References Cited

U.S. PATENT DOCUMENTS

| | | | | |
|---|---|---|---|---|
| 3,589,363 A | * | 6/1971 | Banko et al. ................. | 604/22 |
| 5,026,367 A | * | 6/1991 | Leckrone et al. ...... | 604/101.05 |
| 5,290,279 A | * | 3/1994 | Bonati et al. ................ | 600/108 |
| 5,925,036 A | * | 7/1999 | Maxwell, III ................ | 606/13 |
| 5,989,212 A | * | 11/1999 | Sussman et al. ............ | 604/114 |
| 6,042,586 A | * | 3/2000 | Kawano et al. ............... | 604/19 |
| 6,086,554 A | * | 7/2000 | Humphreys et al. ........ | 285/921 |

\* cited by examiner

Primary Examiner—Teresa Walberg
Assistant Examiner—Vinod D Patel
(74) Attorney, Agent, or Firm—David O'Reilly

(57) ABSTRACT

A system for performing a single portal diagnostic needle arthroscopy and lavage comprised of a handpiece having valves for irrigation and suctioning and a diagnostic cannula attached to the handpiece. An arthroscope is passed through the handpiece and the diagnostic cannula and allows the procedure to be performed through a single port of entry into the interior of the joint. The system includes a mobile cart with a camera and light system and a high-resolution monitor. An air compressor is the pressure source powering the individually controlled irrigation pumps which drive the irrigation fluid through an irrigation hose to the handpiece while a vacuum suction console provides suction for collection of fluid in canisters mounted on the mobile cart. The system includes a biopsy cannula that can be easily exchanged for the diagnostic cannula using an exchange rod. The biopsy cannula is comprised of a pair of piggyback channels, one for visualization, diagnosis, irrigation and suction, while the other is for insertion of a biopsy instrument or other surgical devices. The biopsy instrument is comprised of a thin, approximately 1 mm flexible shaft connected to a forceps configured jaw at the distal end for performing surgical procedures in the joint compartment. A ring handle configuration at the instruments proximal end controls the jaws. Both the diagnostic cannula and biopsy cannula have couplings that include an auxiliary valve for introducing medication and drugs into the joint compartment as well as for removal of sterile synovial fluid.

10 Claims, 8 Drawing Sheets

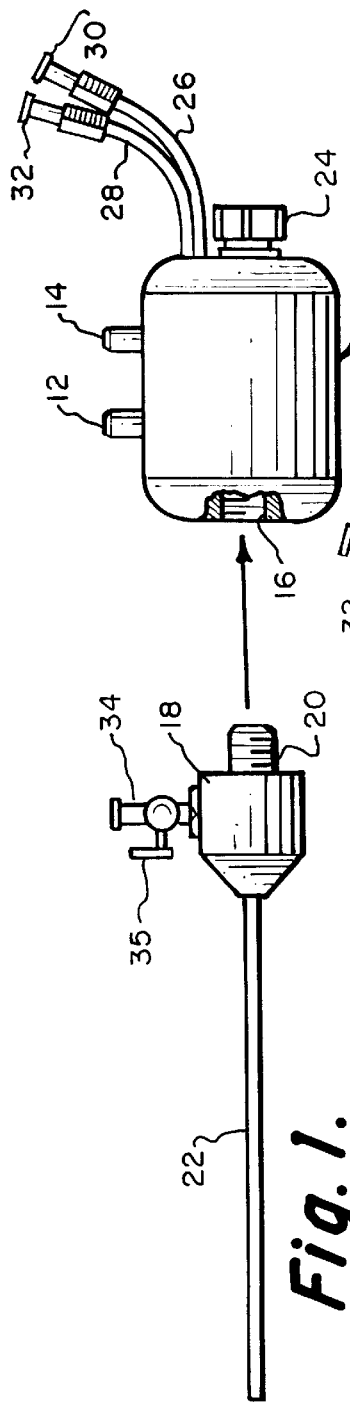
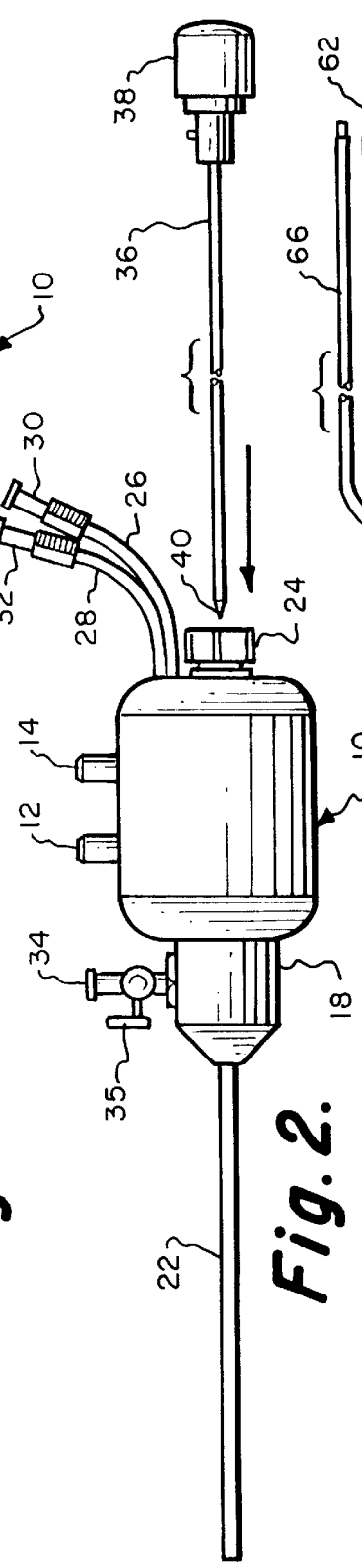
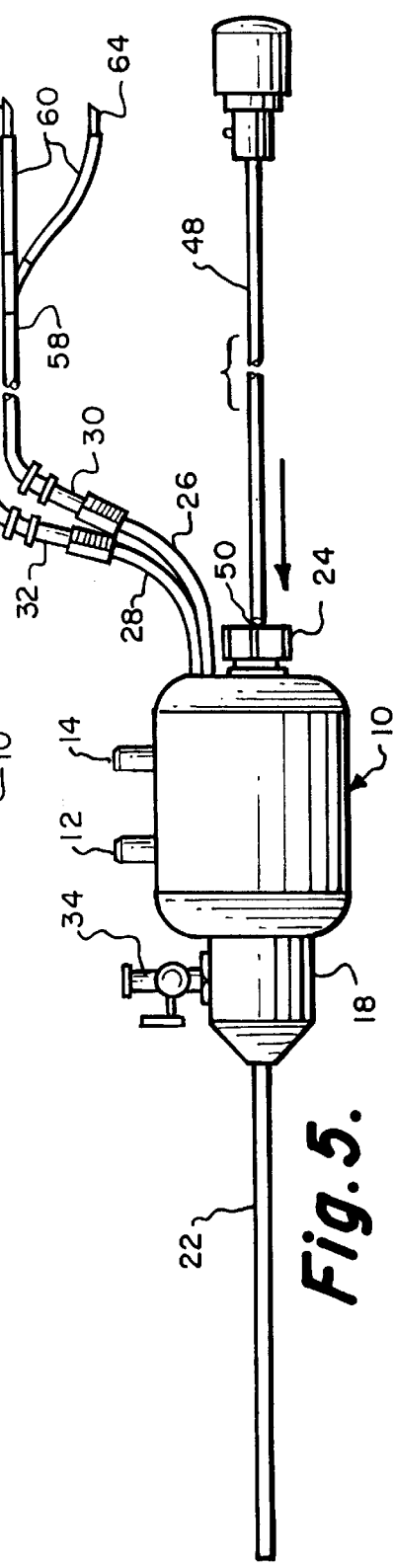

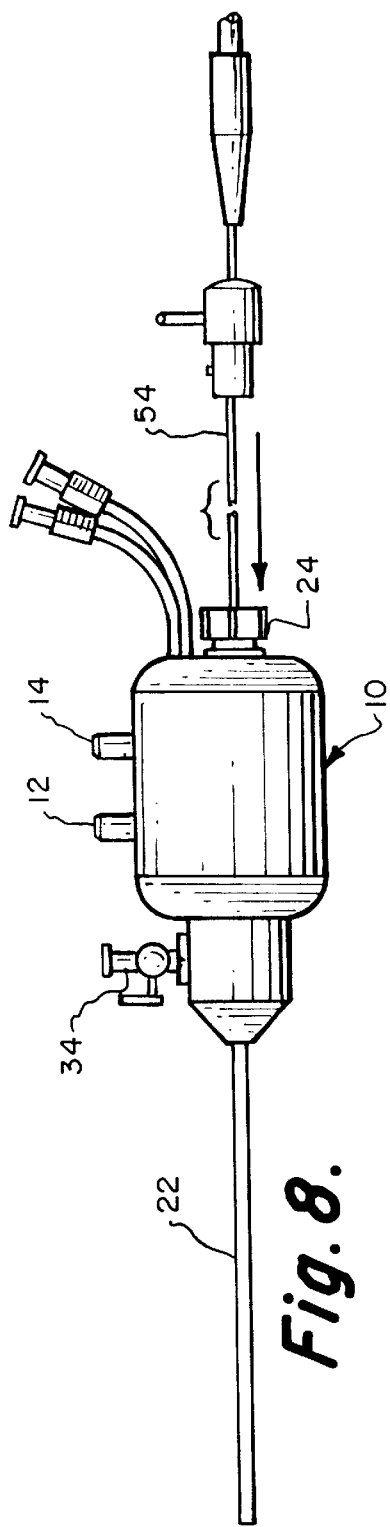
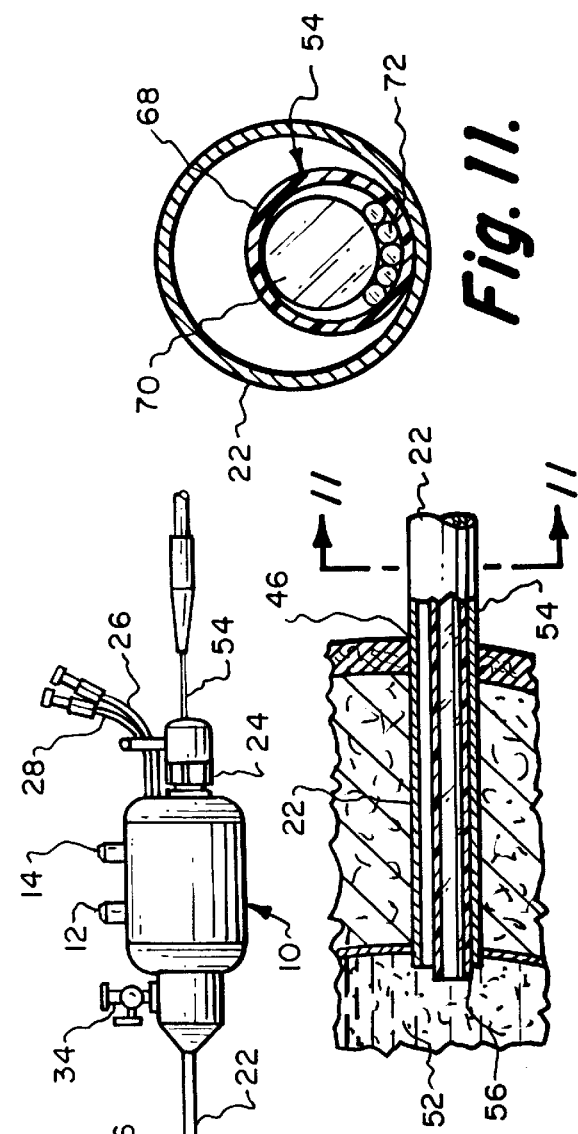
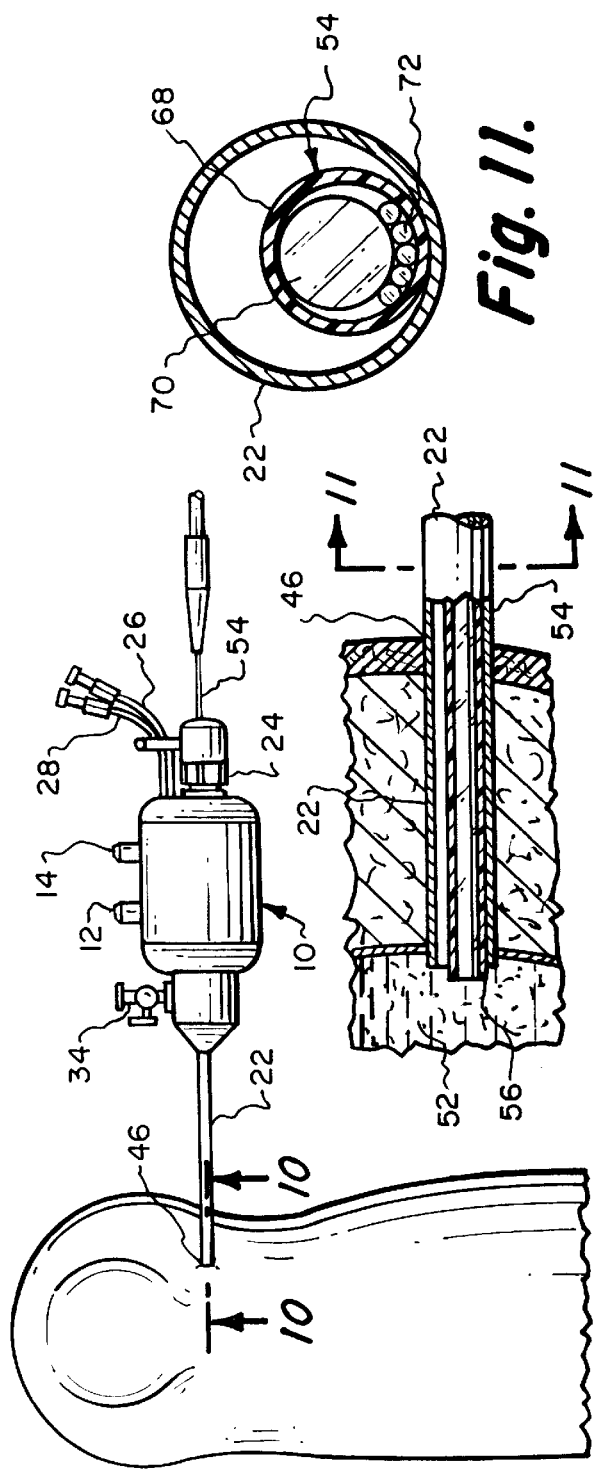

DIAGNOSTIC NEEDLE ARTHROSCOPY AND LAVAGE SYSTEM

CROSS-REFERENCE TO RELATED APPLICATION

This application is a Continuation-In-Part of applicant's co-pending U.S. Pat. Application Ser. No. 09/495,601, filed Feb. 1, 2000.

BACKGROUND OF THE INVENTION

1. Field of the Invention

This invention relates to systems to perform arthroscopies of joints such as the knee and more particularly relates to a diagnostic needle arthroscopy and lavage, (DNAL) system for performing arthroscopies through a single port.

2. Background Information

Arthroscopy is a surgical procedure in which an endoscope (arthroscope) is inserted into a joint. Fluid is then injected into the joint to slightly distend the joint and allow visualization of structures within the joint. Surgery is usually viewed on a monitor so that the whole operating team can visualize the surgical procedure that is being performed. The arthroscopy procedure falls into two types; operative and diagnostic. Operative arthroscopy is more interventional, utilizing larger devices and multiple ports to accomplish a variety of procedures designed to repair internal derangement or tears of intra-articular structures. Diagnostic arthroscopy is less invasive, requiring smaller devices and a single port of entry into the joint. Operative arthroscopes are typically four (4) mm in diameter. The operative arthroscopic procedure is often conducted under general anesthesia and is used to examine and treat the inside of the joint for damaged tissue. Most common types of surgery using operative arthroscopic procedures includes the removal or repair of torn meniscus (cartilage), ligament reconstruction, removal of loose debris and trimming or shaving damaged cartilage. Diagnostic arthroscopy is done under local anesthetic only and is most often accompanied by a thorough rinsing out of the joint (lavage).

The value of arthroscopy as a diagnostic and therapeutic tool is well recognized by physicians. Recent advances have made it technically feasible to perform diagnostic needle arthroscopy procedures in a physician's office using a small, 1.7 mm fiberoptic arthroscope. Generally the diagnostic needle arthroscopy and lavage procedure is used to diagnose and evaluate joint pathology and relieve pain and limited range of motion symptoms from ostheoarthritis that is not relieved by traditional, conservative medical treatment and management. It is also utilized in treating refractory synovitis and determining uncertain etiology. The DNAL procedure has also been found to be an excellent alternative for those patients unable to tolerate the risks of general anesthesia or are unwilling/unable to undergo joint replacement.

Osteoarthritis is a common problem for many middle-aged and elderly people. Osteoarthritis is sometimes referred to as degenerative, or wear-and-tear arthritis, produced by aging. It can also result from a direct injury to the joint. Instability from ligament damage to the cartilage and meniscal injuries cause abnormal wear and tear of the knee joint. Not all cases of ostheoarthritis are related to prior injury however. Research has shown that many are prone to develop osteoarthritis and the tendency may be genetic. Obesity is also a contributory factor. The main problem of osteoarthritis is degeneration of the cartilage that covers articulating surfaces of the joint, resulting in areas of the joint where bone rubs against bone creating bone spurs. Generally osteoarthritis develops slowly over several years. The symptoms are mainly pain, swelling, and stiffening of the joint. As the condition worsens or progresses, pain can interfere with simple, daily activities. Traditional conservative methods of medical treatment include taking anti-inflammatory medication and cortisone injections to reduce the swelling and inflammation of the joint and a variety of pain medications to suppress the bodies pain response. Recently, intra-articular injections of hyaluronic acid, a natural substance found in synovial fluid, has been added to the physician's arsenal in fighting the debilitating effects of OA.

Recently arthroscopic surgeries have been performed in the doctor's office to diagnose and treat a variety of symptoms including osteoarthritis, rheumatoid arthritis, crystal-associated arthritis, and mono-articulate arthritis of unknown etiology. DNAL performed in the physician's office is done under local anesthetic, with the patient awake throughout the procedure. A video monitor is typically used and the patient may observe the procedure if desired. The surgical site is prepared and draped in the appropriate manner and the procedure is performed under sterile conditions. Local anesthesia is injected into the tissue surrounding the surgical site and also into the joint.

The correct placement of an entry port or portal is performed in the usual fashion using the cannula with a sharp trocar inserted to pierce the surface tissue and then a blunt trocar (obturator) to pop through the joint capsule. The blunt obturator is removed from the cannula and the 1.7 mm arthroscope is inserted in its place. Irrigation is performed through the cannula which is connected by tubing to a hanging bag of irrigation solution (sterile saline) under pressure. Infusion of saline is performed until a clear visual field is obtained and is intermittently maintained throughout the procedure.

With the arthroscope inserted in the cannula and a clear field, the compartments of the knee may be visualized and inspected. If biopsy of interarticular tissue is desired or cartilage thickness and quality needs to be evaluated, a biopsy cannula is used to replace the diagnostic cannula and the appropriate instrument used. This is accomplished through the same single port into the joint and under visualization.

The irrigation or lavage of the joint and subsequent aspiration or removal of fluid, removes particulate matter and loose bodies floating in the joint and has been clinically documented in having beneficial effects with regard to pain relief. The flushing of diseased synovial fluid containing irritants, a byproduct of OA, is also therapeutic. By comparison, operative arthroscopy requires a minimum of two larger ports into the joint for biopsy; one for the arthroscope and one for instrumentation. A disadvantage of the present system of operative arthroscopy is the requirement for a second portal for insertion of surgical instruments.

It is therefore one object of the present invention to provide a diagnostic needle arthroscopy and lavage system using a single port entry system allowing the physician to use a minimally invasive, direct visualization approach for diagnosis and also provide therapeutic benefit of complete flushing of the joint with sterile saline (lavage).

Another object of the present invention is to provide a unique proprietary suction/irrigation handpiece that doubles as a diagnostic entry cannula into the joint and also as a housing for a 1.7 mm fiberoptic arthroscope during the procedure. The handpiece also provides suction and irrigation capabilities on demand through finger controlled trumpet valves.

Another object of the present invention is to provide a diagnostic needle arthroscopy and lavage system that permits diagnostic evaluation of a joint along with therapeutic lavage which provides long-term pain reduction/relief by flushing loose bodies and the chemical irritants commonly found in chronic osteoarthritis (OA) and rheumatoid arthritis (RA).

Yet another object of the present invention is to provide a diagnostic needle arthroscopy and lavage system that uses devices of very small size and a single entry port that is an advantage over multiple punctures and larger ports used in standard operative arthroscopy making the procedure ideal for use in a physician's office. With the system disclosed and described, arthroscopic diagnosis and lavage may be performed under local anesthetic only and in conjunction with a mild oral sedative. Patients experience minimum discomfort and generally return to normal activities the next day.

Still another object of the present invention is to provide a diagnostic needle arthroscopy and lavage system that competes with magnetic resonance imaging (MRI) for diagnosing joint disease and derangement. The diagnostic needle arthroscopy and lavage procedure is both diagnostic and therapeutic while the MRI is only diagnostic and does not permit the opportunity to visualize joint pathology, sample tissue, or allow certain interventional treatment modalities.

Direct visualization of joint surfaces and pathology is a superior form of diagnosis when compared to MRI and is also another object of the invention.

Still another object of the present invention is to provide a diagnostic needle arthroscopy and lavage procedure that allows some patients, particularly the elderly, those with heart disease, compromised respiratory function and diabetics, that are not candidates for traditional operative procedures that have the added risk of general anesthesia, to be treated. The system of the present invention provides those patients who have failed conservative medical management and are unable to undergo total or partial joint replacement, a minimally invasive alternative with a high rate of clinically documented success.

BRIEF DESCRIPTION OF THE INVENTION

The purpose of the present invention is to provide a diagnostic needle arthroscopy and lavage system that permits examination and treatment through a single port entry allowing a physician to use minimally invasive, direct visualization approach for diagnosis.

Suction and irrigation have been standard features in operative arthroscopy (joint), laparoscopy (abdomen/pelvis), cystoscopy (bladder), and hysteroscopy (uterus) for several years. Laparoscopy and hysteroscopy currently use carbon dioxide ($CO_2$) gas as the primary distention media which is electrically monitored and controlled. Hysteroscopy also uses fluid as the distention media, similar to operative arthroscopy and cystoscopy. Operative arthroscopy, hysteroscopy, and cystoscopy primarily use irrigation fluid as distention media only, allowing the specific cavity or organ to be extended or open for viewing and performing operative tasks.

The suction and irrigation aspect in laparoscopy uses fluids in a lavage fashion for flushing the cavity/tissue/organ of blood and debris for better visualization, but the distension of the abdomen is accomplished with $CO_2$ gas. Both arthroscopy and laparoscopy require a sharp puncture through tissue to enter the respective cavity while in hysteroscopy, the entry into the uterus is through the vagina and dilation of the cervix and in cystoscopy through dilation of the urethra. No sharp instruments are used in either.

Operative arthroscopy generally has irrigation entering through one port and suction through a second port or through the shaving device introduced through a second port. Hysteroscopy and cystoscopy utilize an outer sheath around the scope which allows the constant inflow and outflow of fluid, preset at specific volume and flow levels and controlled by machine. When fluid is the primarily distention media in hysteroscopy, flow can also be controlled intermittently with the use of a physician operated foot pedal.

The diagnostic needle arthroscopy and lavage system of the present invention is distinguished from the usual system and method described above because both inflow and outflow are intermittent and totally physician controlled by trumpet valve buttons on a handpiece. In laparoscopy the inflow and outflow are intermittently controlled via trumpet valve buttons similar to the system disclosed herein, but the suction/irrigation is accomplished through a separate suction/irrigation device introduced through a second port. The device disclosed herein is a suction/irrigation device that combines separate button valves, physician controlled for both suction and irrigation, and doubling as an entry cannula. It is also the only suction/irrigation device that doubles as the scope cannula and permits a single puncture only.

The diagnostic needle arthroscopy and lavage system is particularly adaptable to performing office-based procedures. The single port entry system allows the physician to use minimally invasive direct visualization for diagnosis and also provide therapeutic benefit by completely flushing the joint with sterile saline (lavage). The single port entry is facilitated through a unique suction/irrigation handpiece which doubles as diagnostic entry cannula into the joint and also as the housing for the small fiberoptic arthroscope during the procedure. Separate irrigation and suction capabilities are incorporated in the handpiece and are physician accessed on demand through finger-controlled trumpet valves.

Disposable suction and irrigation tubing connects the handpiece to the respective dual canister vacuum pump and dual irrigation pump which is pressure controlled via a separate air compressor. These components are mounted on a portable procedure cart which also contains a video system housing the camera, light source, and lensing in a single enclosure. The video system also includes a high-resolution monitor for viewing and professional grade VCR or video printer for documenting the procedure.

Additional capabilities for biopsy under visualization through the single port are accomplished with a separate, unique biopsy cannula which is exchanged with the diagnostic cannula via an exchange rod. The scope is removed from the handpiece and the exchange rod inserted in its place. The diagnostic cannula and attached suction/irrigation handpiece may then be removed leaving only the exchange rod in the joint. The diagnostic cannula is then unscrewed from the front of the suction irrigation handpiece and the biopsy cannula containing a "piggyback" 1 mm working channel attached in its place.

The biopsy cannula and attached suction/irrigation handpiece are then slipped back over the exchange rod and inserted into the joint, eliminating the time-consuming nuisance of finding the original entry path into the joint. The exchange rod may then be removed and replaced with the arthroscope. A 1 mm biopsy forceps is then inserted through the working channel allowing for biopsy under direct visualization. Additional 1 mm devices for use through the working channel of the biopsy cannula permit cutting and shaving/ablation of tissue.

The system disclosed is intended as a diagnostic procedure for joint evaluation while therapeutic lavage provides long-term (6–24 months) pain reduction/relief by flushing out loose bodies and chemical irritants commonly found in chronic osteoarthritis (OA) and rheumatoid arthritis (RA). The small size of the devices (less than half the size of standard, operative arthroscope) and single-entry port rather than multiple punctures and ports in standard operative arthroscopy, make this procedure ideal for a physician's office. The procedure is performed under local anesthetic only and in conjunction with a mild oral sedative (e.g., Valium), eliminating the additional risks and associated complications of general anesthesia or spinal epidural injections. Patients undergoing the procedure experience minimal discomfort and return to normal activities the next day.

At the onset of the procedure a sharp trocar is inserted into the suction/irrigation handpiece and attached diagnostic cannula. The entire device is then inserted into the joint to the level of the joint capsule. The sharp trocar after piercing the surface tissue is replaced with a blunt trocar (obturator) and "popped" into the interior of the joint through the joint capsule. The blunt trocar is removed and replaced with the fiberoptic arthroscope and after attaching the suction/irrigation tubing set; irrigation and aspiration of the joint with sterile saline commences.

The joint is alternately irrigated and suctioned until a clear picture is obtained, the diagnosis is performed while continuing to flush as needed to maintain a clear operative field and to wash out loose bodies and irritants contained within the joint. Generally 1 to 3 liters of saline are used to perform the lavage and to clean the joint of loose debris. Should a biopsy be desired, the procedure for exchanging diagnostic and biopsy cannula can be used.

The diagnostic and biopsy cannula are attached to a threaded coupling or fixture that includes a stopcock or ball valve that allows for removal of sterile synovial fluid and loose bodies, and also permits direct injection of anesthetic or drugs, into the joint. The invention disclosed herein is the only application of an additional valve on the suction/irrigation device which is different from the large number of standard entry trocar/cannula that utilize a valve for distention purposes only.

The system also includes the use of video coupling optics connected to the camera head, and light source in a single unit located off the sterile field. This eliminates the need to have a camera head and cable, optical coupler, light cable and scope all sterilized and assembled on the field. The only video train component in this system disclosed herein needing sterilization is the fiberoptic scope which contains integral illumination fibers. The 1.7 mm scope in this system uses a 30,000 pixel fiber image bundle with a two-element distal lens which provides the image quality, large field of view, and depth of field approaching that of a 4 mm rod lens arthroscope.

Other objects, advantages, and novel features of the invention will become apparent from the following detailed description when considered in conjunction with the accompanying drawings where in like reference numbers and identifying light parts throughout.

BRIEF DESCRIPTION OF THE DRAWINGS

FIG. 1 is a plan view of a handpiece for use in diagnostic needle arthroscopy and lavage system illustrating the connection of the diagnostic cannula.

FIG. 2 is a plan view illustrating the insertion of a sharp trocar through the handpiece and diagnostic cannula for piercing the skin and surface tissue directly above the joint being entered.

FIG. 5 is a plan view illustrating the replacement of the sharp trocar with the blunt trocar (obturator) for puncturing the joint capsule.

FIG. 8 is a plan view of the diagnostic needle arthroscopy and lavage handpiece with the diagnostic cannula attached illustrating insertion of the arthroscope.

FIG. 9 illustrates the diagnostic cannula in the knee joint with the arthroscope locked in position.

FIG. 10 is a sectional view taken at 10—10 of FIG. 9 illustrating the diagnostic cannula in the joint and the arthroscope extending slightly beyond the end of the cannula.

FIG. 11 is a sectional view taken at 11—11 illustrating the distal, circumferential structure of the diagnostic cannula and arthroscope. The distal optics of the arthroscope are also illustrated.

DETAILED DESCRIPTION OF THE INVENTION

Figures 3, 4:
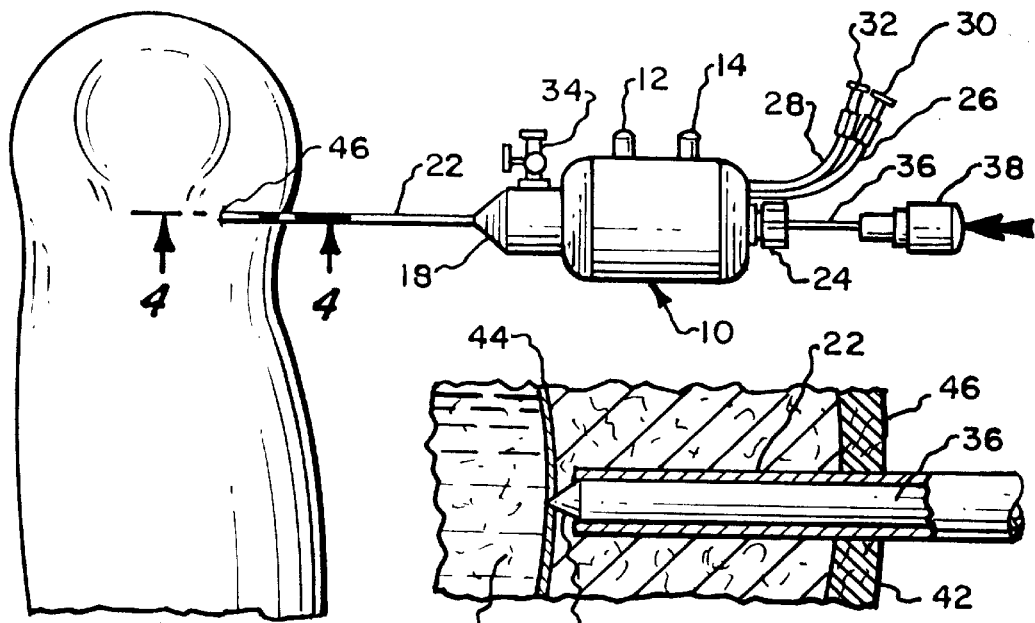
FIG. 3 is a plan view illustrating the insertion of the handpiece with a trocar through the surface tissue of the knee joint with the sharp trocar locked in place and penetrating the tissue to the depth of the joint capsule.
FIG. 4 is a partial sectional view taken at 4—4 illustrating the sharp trocar locked in place in the diagnostic cannula piercing the surface tissue.

The diagnostic procedure components of the system are illustrated in FIG. 1 and are comprised of a handpiece 10 having trumpet valves 12 and 14 and threaded socket 16 for receiving coupling 18 having threaded nipple 20 and a diagnostic cannula 22. Threaded nipple 20 is threaded into socket 16 in cylindrical handpiece 10 to secure diagnostic cannula 22 to handpiece 10. Fitting 24 on the opposite end of handpiece 10 receives instruments to pass through handpiece 10, coupling 18 and diagnostic cannula 22 as shown in FIGS. 2 through 10. Handpiece 10 also has irrigation and suction channels 26 and 28 having fitting or luers 30 and 32 for quickly attaching irrigation and suction tubing. A unique feature of the invention is the inclusion of an auxiliary stopcock or ball valve 34 attached to coupling 18 which may be used for direct medication into the joint and/or sterile synovial fluid removal which will be described in greater detail hereinafter.

The placement of the diagnostic cannula of the DNAL system is illustrated in FIGS. 2 through 7. Initially an introducer in the form of a sharp trocar 36 having handle 38 is inserted into fitting 24 in handpiece 10 and passed through channel 15 (FIG. 12) into cannula until the sharp tip 40 extends out of diagnostic cannula 22 as illustrated in FIG. 4. Sharp trocar 36 is used to pierce the skin 42 and surface tissue directly above the joint at the point of insertion until it reaches the joint capsule 44, creating entry portal 46.

Figures 6, 7:
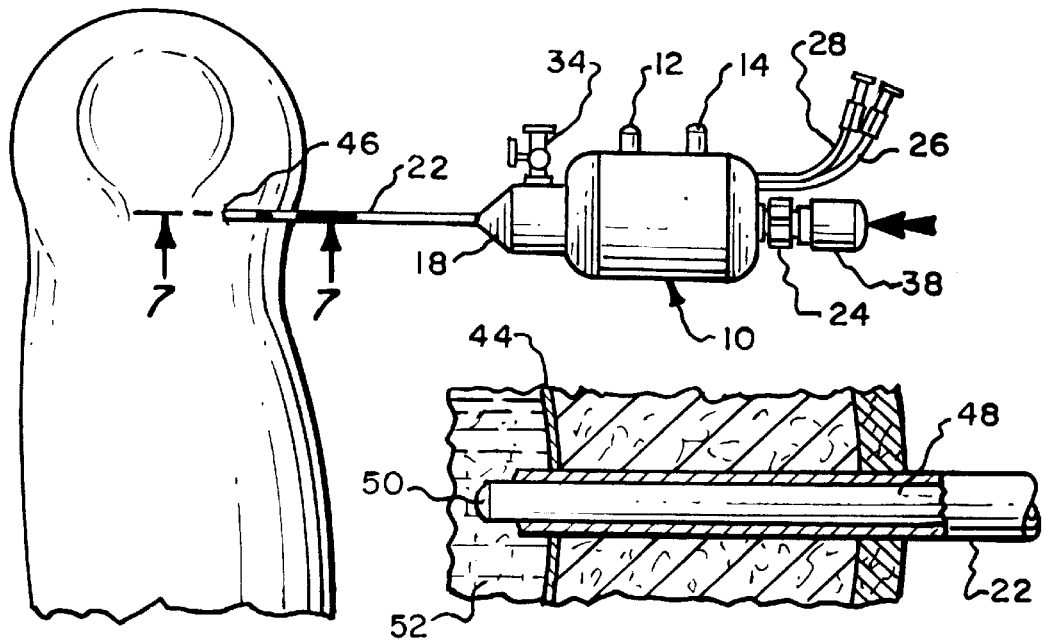
FIG. 6 illustrates the insertion and locking in place of the obturator through the diagnostic cannula.
FIG. 7 is a partial section illustrating the obturator in the diagnostic cannula penetrating the joint capsule and inside the joint space.

FIG. 3 illustrates placement of the diagnostic needle arthroscopy and lavage system in a knee joint but, of course, the system may be used for other joints as well. After diagnostic cannula 22 with sharp trocar 36 reaches joint capsule 44, sharp trocar 36 is withdrawn and replaced with blunt obturator 48 having a blunt end 50. Blunt obturator 48 is passed through fitting 24 in handpiece 10 and diagnostic cannula 22 as shown in FIGS. 6 and 7. With diagnostic cannula 22 in portal 46, blunt trocar 48 pushed (i.e. "popped") through joint capsule 44 into interior joint space 52. Diagnostic cannula 22 is now positioned in interior joint space 52 ready for use in examining the joint.

An arthroscope 54 is then inserted through and locked into fitting 24 in handpiece 10 into diagnostic cannula 22 and extends slightly beyond the distal end of diagnostic cannula as illustrated in FIG. 10. The entire diagnostic cannula 22 may now be extended through portal 46 deep into joint compartment 52 with fiberoptic arthroscope extended at 56 to view and inspect all compartments such as the superpatella pouch, patellofemoral joint space, medial recess, medial compartment, intercondylar notch, lateral compartment, and lateral recess. During the inspection and examination, the joint is distended by injecting an irrigation solution through hose 58 (FIG. 5). The "Y" shaped end 60 of irrigation hose 58 has spikes 62 and 64 for puncturing a seal on irrigation solution (sterile saline) bags (not shown). Irrigation solution is released through irrigation and suction handpiece 10 by operation of trumpet valve 12. The irrigation fluid distends joint space 52 allowing visualization of the interior of the joint.

Direct insertion of medication into the interior joint space and/or removal of sterile synovial fluid may be performed through auxiliary ball valve 34. Medication is inserted by opening auxiliary ball valve 34 by rotating handle 35 providing an entry/exit path through fitting or coupling 18 into diagnostic cannula 22. Medication can then be injected through ball valve 34 into the interior joint space 52. Alternatively, an empty, sterile syringe can be attached to the end of ball valve 34 for removal of sterile synovial fluid for biopsy.

The diagnostic procedure is performed by visualizing the interior joint space 52 through arthroscope 54 while irrigating the joint cavity with sterile saline solution through irrigation tubing 58, connected to luer fitting 30 and through irrigation tube 26 by operating trumpet valve 12 to distend the joint. This fills and distends the joint allowing visualization of interior joint space 52 through fiberoptic arthroscope 54. Distal end 56 of arthroscope 54, locked in position in handpiece 10, may be manipulated by moving handpiece 10 around to visualize the inside of interior joint space 52.

After irrigation and distention, suction may be applied by operating trumpet valve 14, through suction channel 28 and luer 32 connected to suction tube 66 (FIG. 5) flowing to dual suction collection canister as will be described in greater detail hereinafter. The irrigation and suction system is used to remove loose bodies, debris and other irritants contained within a diseased joints interior joint space 52. Removal of loose bodies, debris and irritants is found to be beneficial particularly to those suffering from osteoarthritis.

Arthroscope 54 is a small (approximately 1.7 mm) stainless steel sheath 68 (FIG. 11) containing a 30,000 pixel fiberoptic image bundle and having a distal glass lens 70 for viewing the interior of joint space 52 with a CCD camera. Optical fibers 72 contained in sheath 68 are provided for illuminating joint space 52 with high-intensity light. The outside diameter of 35 fiberoptic arthroscope 54 is approximately ½ the inside diameter of diagnostic cannula 22. This allows larger pieces of cartilage or debris in joint space 52 to be suctioned out through cannula 22 without removing fiberoptic arthroscope 54.

Figure 12A:
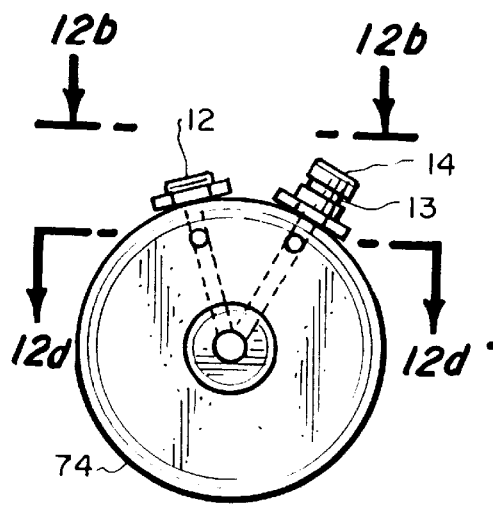
FIGS. 12(a) and (b) are an end view and top view respectively showing the orientation of the irrigation and suction valves.
Figure 12B:
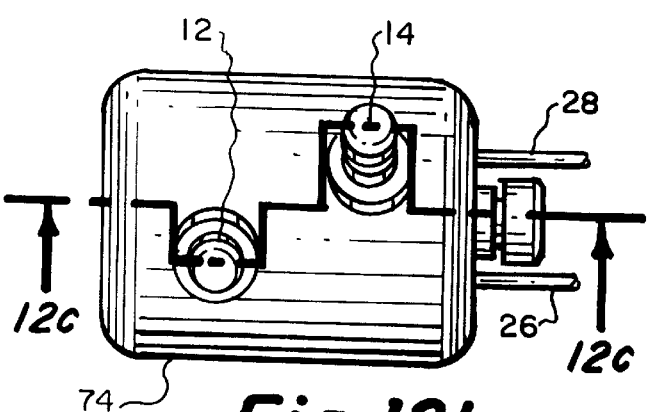
FIG. 12(c) is a cross-sectional view taken at 12(c)—12(c) of FIG. 12(b) illustrating the operation of the irrigation and suctioning valves.
FIG. 12(d) is a partial sectional view taken at 12(d)—12(d) of FIG. 12(a) illustrating the configuration of the valves and their respective flow channels.
FIG. 12(e) is a partial sectional view illustrating valve locking mechanisms.

The details of the irrigation, suctioning, and manipulating handpiece 10 are illustrated in FIGS. 12(a) through 12(d). FIGS. 12(a) and 12(b) are an end view and top view respectively illustrating the orientation of trumpet valves 12 and 14 in handpiece 10. Trumpet valves 12 and 14 are radially offset from each other about 15° to 20° on either side of a center line through handpiece 10. This ergonomic arrangement permits handpiece 10 to fit comfortably in the hand of a physician with the index and middle fingers conveniently resting on trumpet valves 12 and 14. The offset also assists the surgeon in distinguishing which is the suction valve and which is the irrigation valve. Suction valve 14 also includes circumferential groove 13 to prevent the valves from being interchanged when re-assembled after being disassembled for cleaning and sterilization. This assures that no cross-contamination can occur by preventing the installation of an improperly cleaned and sterilized suction valve stem 86 in the irrigation valve port when re-assembling the handpiece.

Figure 12C:
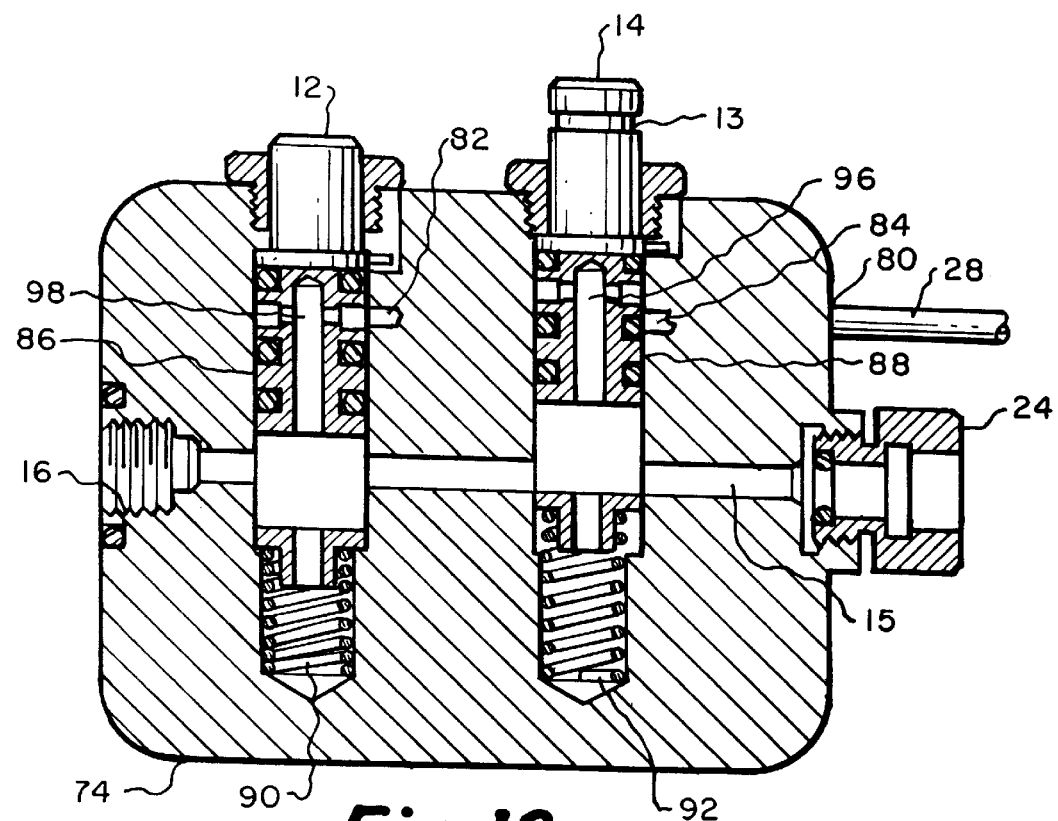
Figure 12D:
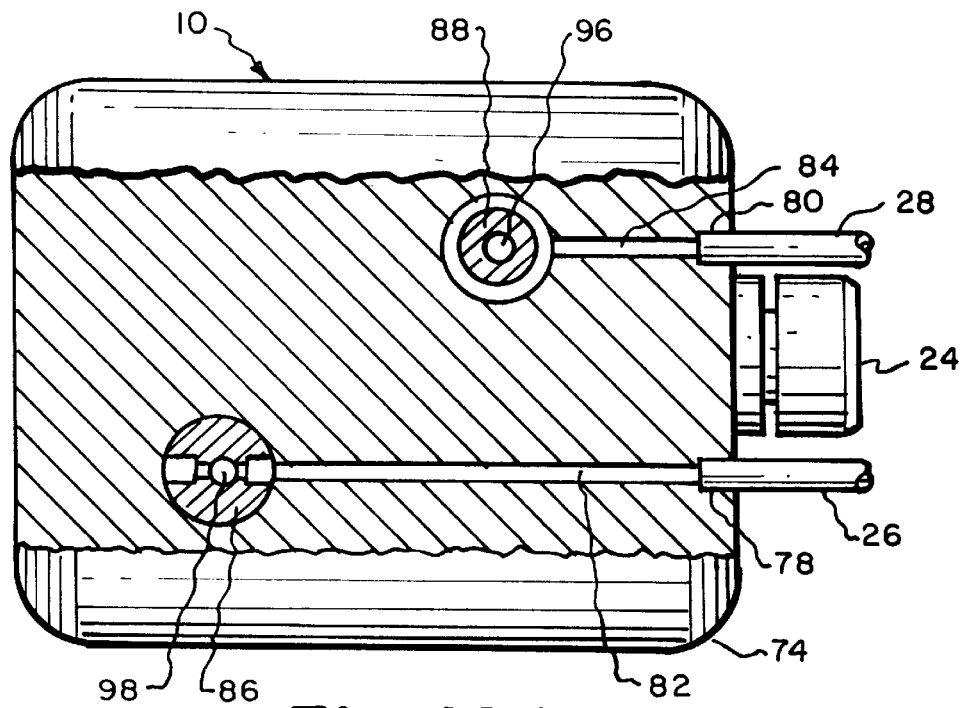
Figure 12E:
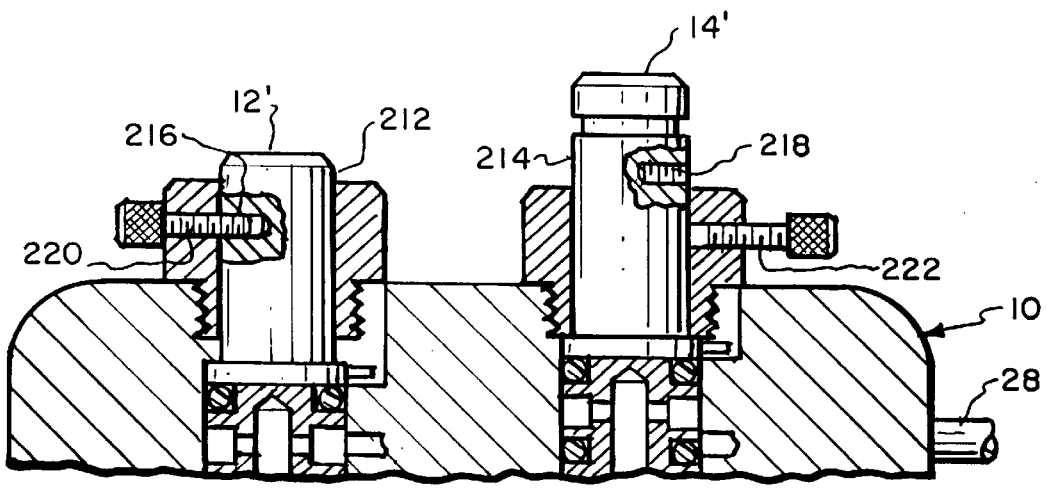
Figure 13:
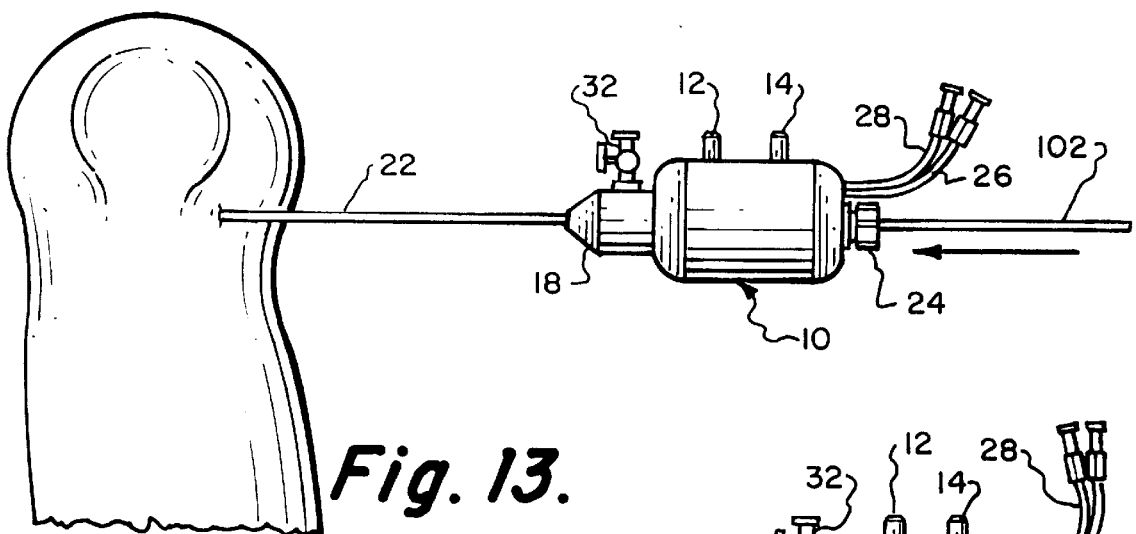
FIG. 13 is a plan view illustrating the insertion of an exchange rod for removing and exchanging the diagnostic cannula.

As shown in FIGS. 12(c) and 12(d) irrigation and suctioning handpiece 10 is comprised of a main housing 74, preferably made of aluminum, having an interior passageway 15 connecting fitting 24 with threaded socket 16. Irrigation and suctioning channels 26 and 28 respectively (FIG. 12(d)) are connected through ports 78 and 80 to passageways 82 and 84 to control the flow of irrigation and suctioned fluids through trumpet valves 12 and 14 and through diagnostic cannula 22.

Trumpet valves 12 and 14 are comprised of stems 86 and 88 biased by springs 90 and 92 into a normally closed position. Pressing down on either of trumpet valves 12 and 14 connects passageway 15 through valve stems 86 or 88 to either of passageways 82 or 84. This construction allows the physician to manipulate the diagnostic cannula 22 by moving handpiece 10 around and injecting irrigating saline into, or suctioning fluid from joint space 52 as desired.

Irrigating fluid is supplied by pressing trumpet valve 12 to connect interior passageway 98 in valve stem 86 to passageway 82. This allows irrigating fluid to flow from irrigating channel 26 into diagnostic cannula 22 through main passageway 15. Suction is provided in the same manner with irrigation trumpet valve 12 in the up, or closed position.

When suction trumpet valve 14 is depressed, passageway 84 is connected through passageway 96 in valve stem 88 to main passageway 15. This allows material to be suctioned from joint space 52 through handpiece 10 to collecting canisters as will be described in greater detail hereinafter. Thus the unique construction of irrigating and suction handpiece 10 allows the physician to visualize the interior of joint space 52 while irrigating and suctioning alternately as desired.

Figure 14:
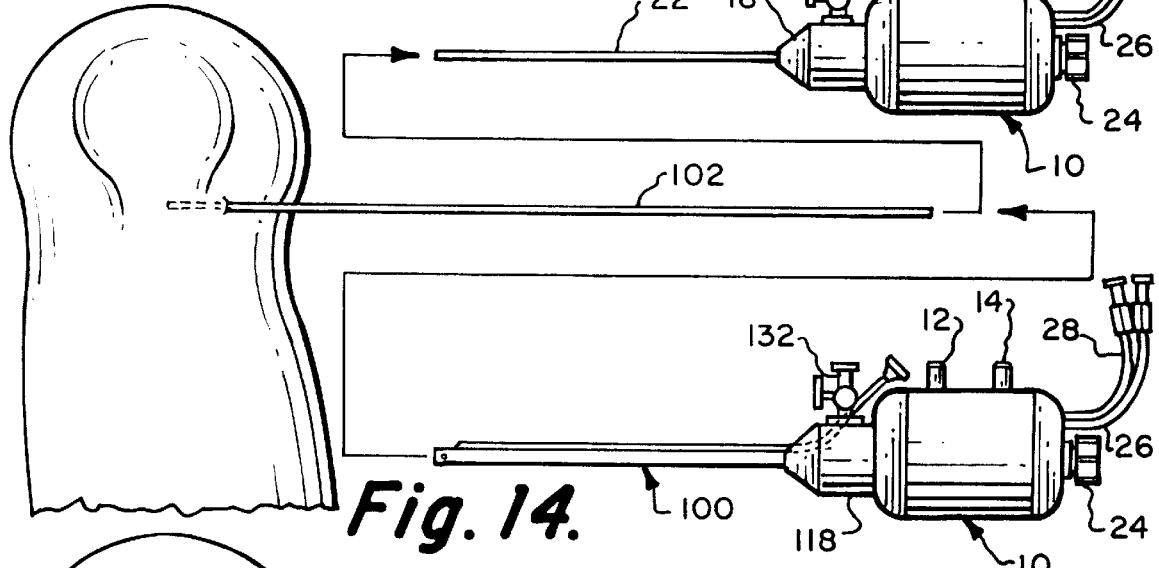
FIG. 14 illustrates the removal of the diagnostic cannula and replacement with the biopsy cannula using the exchange rod.

Another unique aspect of the invention is the ability to perform biopsies and other surgical functions through irrigating and suctioning handpiece 10 by exchanging the diagnostic cannula 22 for a biopsy cannula 100 as shown in FIG. 14. This procedure is facilitated by use of an exchange rod 102 that is passed down through fitting 24 on handpiece 10 though diagnostic cannula 22 until it is inside knee joint space 52. Diagnostic cannula 22 may then be withdrawn with handpiece 10 as shown in FIG. 14. Diagnostic cannula 22 may then be removed by detaching coupling 18 from handpiece 10 as illustrated in FIG. 1.

Figure 15:
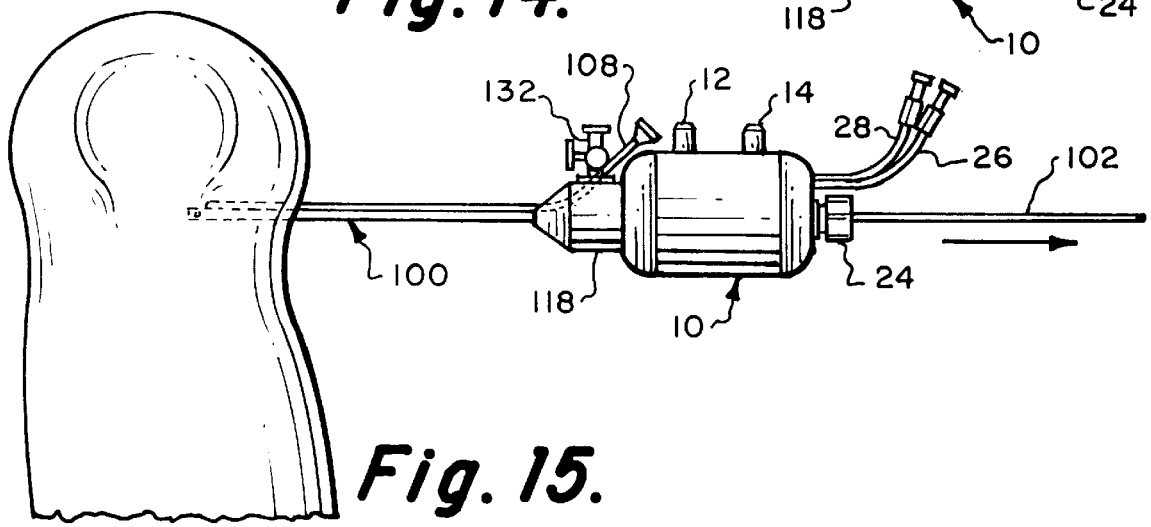
FIG. 15 is a plan view illustrating the removal of the exchange rod after placement of the biopsy cannula into the joint.
Figure 16:
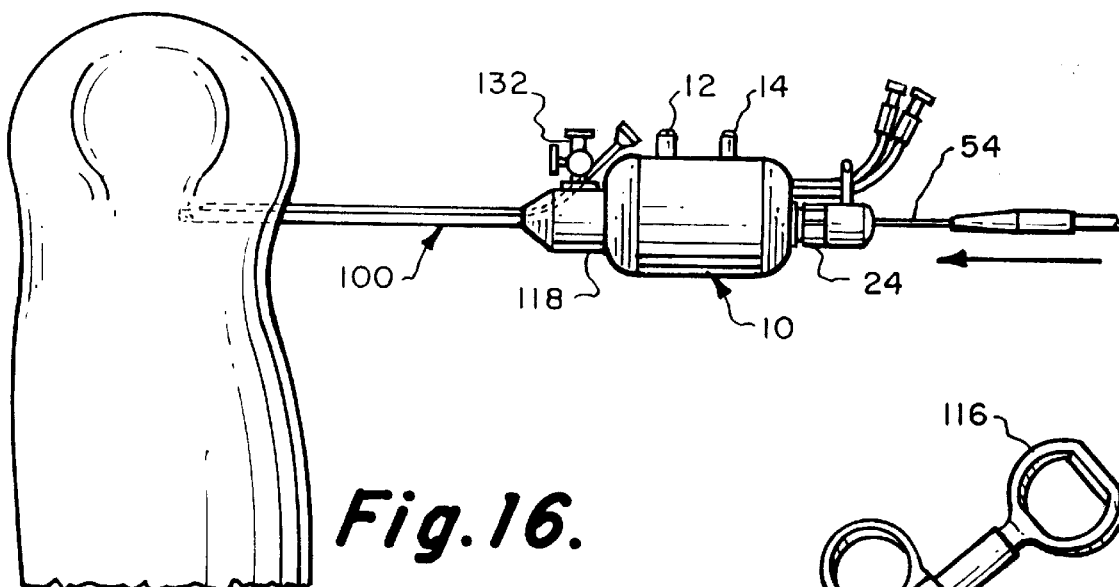
FIG. 16 illustrates the placement of the arthroscope into and through the biopsy cannula.
Figure 17:
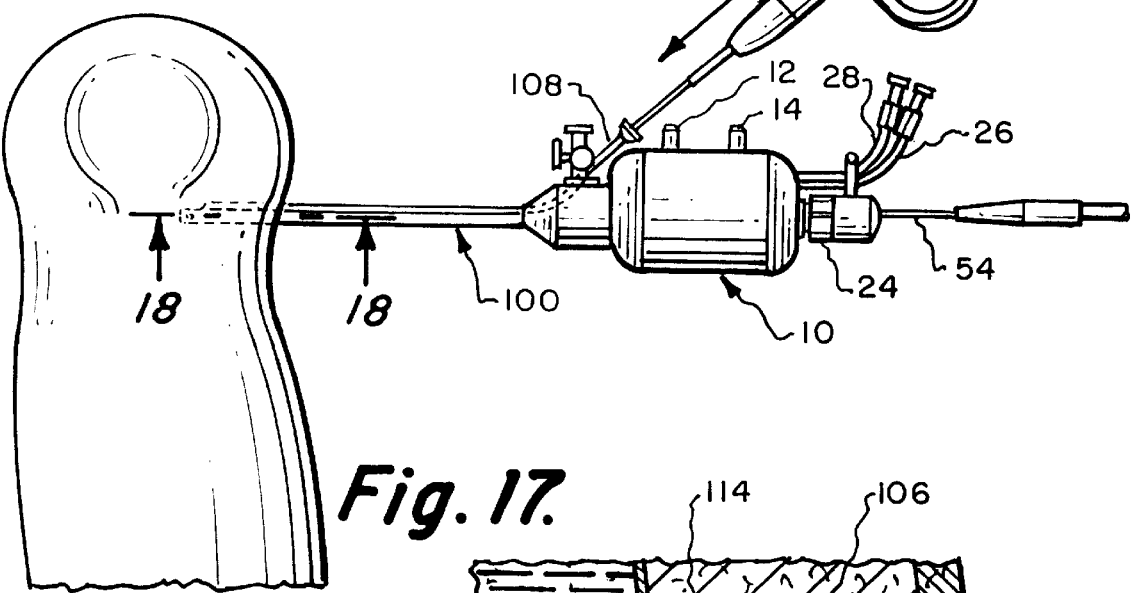
FIG. 17 illustrates the insertion of the 1 mm biopsy instrument into and through the working channel of biopsy cannula.
Figure 18:
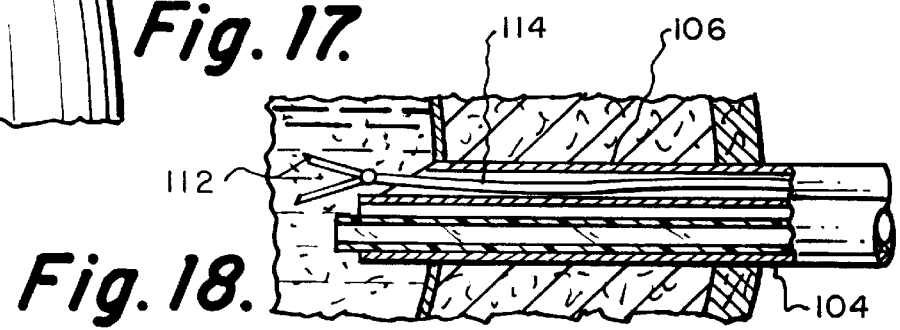
FIG. 18 illustrates a sectional view of the biopsy cannula with biopsy instrument and arthroscope in place and inside the joint capsule.

Biopsy cannula 100 is then attached to handpiece 10 by coupling 118 which also has integral stopcock or ball valve 132 for addition of internal joint medication with a syringe, or removal of sterile synovial fluid if desired. Biopsy cannula 100 is then fed over exchange rod 102 into joint space 52 and exchange rod 102 withdrawn as illustrated in FIG. 15 leaving biopsy cannula 100 in place. Biopsy cannula 100 may now be used for performing surgical procedures, under visualization, such as biopsies as illustrated in FIGS. 16 through 18.

With biopsy cannula 100 in place, arthroscope 54 is inserted through fitting 24 of handpiece 10 into the joint space 52 as before. As can be seen more clearly in FIG. 18, biopsy cannula 100 is comprised of a pair of "piggyback" (i.e. side by side) cannulas comprised of a main diagnostic cannula 104 and instrument channel 106. Diagnostic cannula 104 allows visualization, suction and irrigation to be performed as before. Biopsy cannula has an open fitting 108 at the proximal end for receiving a surgical tool or instrument 110 such as biopsy forceps. Forcep jaws 112 at the distal end of flexible shaft 114 connected to surgical instrument 110 is operated by manipulating ring handle 116. Forcep jaws 112 can be used to break up larger pieces of debris that might not fit through diagnostic cannulas 22 or 104 or can be used to bite and remove sample tissue from interior joint space 52.

The use of biopsy cannula 100 to perform biopsies with a biopsy forcep of approximately 1 mm in size is inserted through working channel 106 allowing biopsies to be performed under direct visualization through arthroscope 54. Additional 1 mm devices for performing the tasks of cutting, shaving and ablation through working channel 106 are available. The use of exchange rod 102 eliminates the time-consuming nuisance of finding original entry path 46 into interior joint space 52 adding an additional level of safety by eliminating the need to create a new entry path with the sharp trocar. While the system is described as performing an irrigation and lavage first and biopsy second, of course, the steps could be reversed or one used without the other. That is, the system can be used for a biopsy first followed by an irrigation and lavage or could be used to perform a biopsy or an irrigation and lavage separately, if desired.

The diagnostic system allows alternate irrigation and suctioning until a clear picture is obtained through the arthroscope and displayed on a monitor as will be described hereinafter. While examination and diagnosis are performed, continuous flushing is needed to maintain a clear operative field and to wash out loose bodies and irritants contained within the interior joint space 52. Generally up to 3 liters of sterile saline are used to perform the lavage and flush joint space 52. Should a biopsy be desired, the procedure for exchanging diagnostic and biopsy cannula as described hereinabove is employed.

Both inflow and outflow are intermittent and totally physician controlled via trumpet valve buttons 12 and 14 on irrigation and suctioning handpiece. Additional capability of continuous irrigation or suction without physically holding down the individual trumpet valve may be accomplished through the use of a special locking valve nut and locking screw, if desired as will be described in greater detail hereinafter. The separate irrigation and suctioning capability incorporated in handpiece 10 are very efficient as they are physician accessed on demand through the finger control trumpet valve while manipulating handpiece 10. In prior art devices and surgical procedures such as in laparoscopy, the inflow and outflow by irrigation and suctioning is accomplished through separate suction and irrigation devices introduced through a second port. With the device disclosed herein, the suction and irrigation is both the distention media and also the primary therapy. The device is unique as it combines separate physician controlled button valve for both irrigation and suction while doubling as an entry cannula and a scope cannula and permits a single puncture or port entry.

The use of the auxiliary stopcock or ball valve on the front coupling of the diagnostic and biopsy cannulas allow for removal of sterile synovial fluid and loose bodies and direct injection of anesthetic and medication into the interior joint space 52. The inclusion of the stopcock and ball valve allows for the unique function of uninterrupted irrigation and suctioning on a larger scale, while also allowing addition of anesthetics and removal of sterile samples/biopsy through the additional valve located on both diagnostic cannula 22 and biopsy cannula 100.

Figure 19:
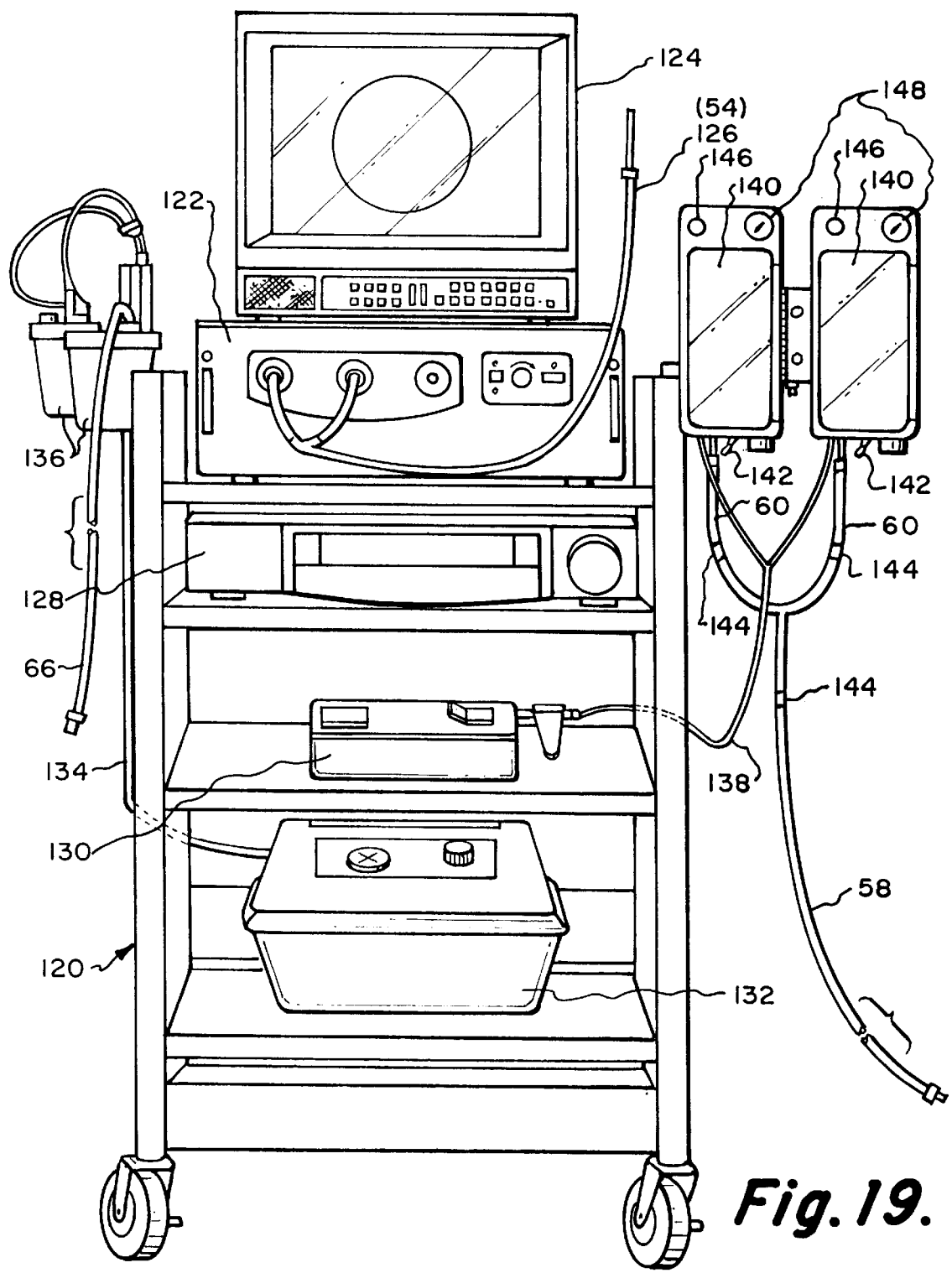
FIG. 19 illustrates the DNAL procedure cart housing the video monitor, camera, optic and light system, VCR, air compressor and dual irrigation pump, suction unit and dual collection canisters with suction and irrigation tubing attached and proximal arthroscope inserted into the separate optical and illumination receptacles on the front of the video system.

The entire operating system for visualization, irrigation, and suction as well as recording the procedure is mounted on a mobile self-contained cart for ease of movement and storage with a small footprint for use in a confined office environment. The support system for the diagnostic needle arthroscopy and lavage system is illustrated in FIG. 19. Portable cart 120 has shelves for receiving the components that work with the diagnostic system shown in FIGS. 1 through 18. A CCD camera, camera head, light source, optical coupling lens and focusing mechanism are all contained within console 122 which is mounted on the top shelf of portable cart 120 along with a high-resolution monitor 124. Console 122 is directly connected to arthroscope 54, 126 in FIG. 19, having distal lens 70 and light conducting fibers 72 as illustrated in FIG. 11.

A standard, professional grade, broadcast quality VCR 128 is provided for recording and documenting the procedure. Irrigation pressure is provided by air compressor 130 and controlled by irrigation pumps 140. Vacuum suction is controlled by console pump 132. Vacuum suction console is connected by a vacuum pipe 134 to collection canisters 136 mounted on the side of cart 120. Collection canisters 136 are connected to suction channel luer 32 on suction channel 28 on handpiece 10 by suction hose 66 as shown in FIG. 5.

Compressor 130 provides forced air through tubing 138 to dual irrigation pumps 140 each pressurizing 1 liter bags of sterile saline. Sterile saline bags are connected to irrigation channel 26 through luer 30 on handpiece 10 by irrigation hose 58 that bifurcates into two tubes 60 with integral bag spikes 62 and 64. Irrigation pumps 140 each have a switch 142 for selecting one or the other of the pumps to be pressurized. This allows empty saline solution in one pump to be replaced while the flow is being delivered from the other pump. Separate pressure controls 146 and pressure gauges 148 are contained on pumps 140 for precise pressure control. Hose clamps 144 on hoses 60 also close and prevent the flow of solution to hose 58. A single hose clamp 144 on hose 58 prevents flow to suction irrigation handpiece 10.

A unique advantage of this system and its concept is the optical coupler, focusing mechanism, CCD camera, camera head and light source are all contained in one unit located away from the sterile field. The only optical/visualization component requiring sterilization is the arthroscope (54, 126 in FIG. 19). Other components of the DNAL system used within the sterile field are the disposable irrigation and suctioning hoses 58 and 66, handpiece 10, diagnostic and biopsy cannulas 22 and 100 along with sharp trocar 36, blunt obturator 48, exchange rod 102 and biopsy instrument 110.

To perform the DNAL procedure, diagnostic cannula 22 is placed in interior joint space 52 as illustrated in FIGS. 1 through 7. Irrigation and suctioning hoses 58 and 66 may then be connected to irrigation and suction channels 26 and 28 on handpiece 10 and fiberoptic arthroscope 54 inserted through diagnostic cannula 22. Alternately irrigation and suctioning is provided until a clear picture is obtained on monitor 124. Examination and diagnosis is performed while continuing to flush as needed by manipulating irrigation and suctioning trumpet valves 12 and 14 to maintain a clear operative field. Suctioning trumpet valve 14 is operated to flush out loose bodies and debris as well as irritants contained in joint space 52.

Generally up to 3 liters of sterile saline are used to perform the lavage and clean interior joint space 52. Biopsies and limited surgical procedures can then be performed by exchanging diagnostic cannula 22 for biopsy cannula 100 as illustrated in FIGS. 13 through 18. With arthroscope 54 in place through diagnostic channel 104 of biopsy cannula 100, a surgical instrument approximately 1 mm in diameter may be passed through working channel 106 to perform minor biopsies with forcep jaws 112. Cutting, shaving and ablation applications can also be accomplished through channel 106. The entire procedure is performed using only a single, small entry port which minimizes trauma to the patient. The single puncture wound is dressed and covered with a simple bandage.

Another embodiment is illustrated in FIG. 12(*d*). In some cases it might be advantageous to be able to lock irrigation valve 12 or suction valve 14 in an on position. One method of locking these valves in an on position is illustrated in FIG. 12(*e*). Each plunger 212 and 214 of the irrigation and suctioning valves 12' and 14' would have an aperture 216 and 218 threaded to receive a threaded pin 220 and 222. FIG. 12(*e*) shows irrigation valve 12' locked in an on position and suctioning valve 14' in an unlocked closed position. Either one of irrigation and suctioning valves 12' and 14' respectively can be locked in an on position by engaging aperture 216 or 218 with threaded pin 220 or 222. Irrigation valve 12' is shown in an on and locked position with threaded pin 220 engaging aperture 216 in plunger 212. This will maintain a flow of irrigating fluid to the interior of the joint. Likewise, suctioning valve 14' can be in an open and locked position by engaging pin 222 with aperture 218 after plunger or stem 214 has been pushed downward. Other methods of locking one or the other valve in an on position could be used such as a push-push pin having a spring loaded mechanism to disengage the pin from the valve stem.

Thus there has been disclosed a unique and novel diagnostic needle arthroscopy and lavage system that uses only a single point of entry for performing diagnostic and therapeutic procedures. The system includes a handpiece having valves for simultaneously manipulating a diagnostic or biopsy cannula while performing irrigation and suctioning to wash out and remove any debris, loose bodies, as well as irritants contained within the joint. The system also includes a biopsy cannula that can be easily exchanged by use of an exchange rod. The biopsy cannula also allows for both irrigation and suctioning as well as biopsies to be performed with a biopsy instrument inserted through an adjacent working channel. In addition, both diagnostic and biopsy cannulas have the ability to separately infuse medication and remove sterile synovial fluid through the additional stopcock valve located on couplings 18 and 118.

This invention is not to be limited by the embodiment shown in the drawings and described in the description which is given by way of example and not of limitation, but only in accordance with the scope of the appended claims.

What is claimed is:

1. A method for diagnostic examination and therapeutic treatment of joint diseases through a single entry portal comprising;

connecting a handpiece having a central passageway and irrigation and suctioning valves to a diagnostic cannula;

inserting a sharp trocar through said handpiece into said diagnostic cannula;

piercing said joint with said sharp trocar to provide a single portal of entry into said joint;

removing said sharp trocar and inserting a blunt obturator through said handpiece and said diagnostic cannula;

inserting said diagnostic cannula with said blunt obturator through a capsule of said joint;

removing said blunt obturator and inserting an arthroscope through said handpiece and diagnostic cannula through said single entry portal into said joint;

connecting an irrigating fluid to said handpiece;

connecting a source of suction to said handpiece;

intermittently delivering irrigating fluid to said joint interior and suctioning out fluid to remove debris from said joint;

whereby a physician can visualize, diagnose, and treat a diseased joint.

2. The method according to claim 1 in which said intermittent irrigation and suctioning of fluid is performed by trumpet valves in said handpiece.

3. The method according to claim 1 including;

interchanging said diagnostic cannula with a biopsy cannula having side by side cannulas for insertion of an arthroscope and surgical biopsy tool.

4. The method according to claim 1 including administering medication and suctioning a sterile synovial fluid and loose bodies from joint compartment through an auxiliary valve in said handpiece.

5. The method according to claim 1 including illuminating said joint compartment through integrated illumination fibers in said arthroscope directly connected to an optical coupler, camera head, CCD camera and a light source.

6. The method according to claim 1 including exchanging said diagnostic cannula for a biopsy cannula inserted into said joint compartment.

7. The method according to claim 6 including introducing surgical instruments through a channel that is parallel to a diagnostic channel in said biopsy cannula.

8. The method according to claim 1 including connecting an arthroscopic camera to said arthroscope; displaying the output of said arthroscopic camera on a high resolution monitor.

9. The method according to claim 4 including collecting said suctioned synovial fluid and loose bodies in a pair of canisters; controlling said suction by a suction trumpet valve in said handpiece.

10. The method according to claim 8 including recording the output of said arthroscopic camera in a video recorder.

* * * * *